United States Patent [19]

Shimamura et al.

[11] 4,296,051

[45] Oct. 20, 1981

[54] METHOD OF PRODUCING GRANULAR SODIUM DICHLOROISOCYANURATE

[75] Inventors: Tadao Shimamura; Tadayoshi Kojima, both of Tokushima, Japan

[73] Assignee: Shikoku Kasei Kogyo Co., Ltd., Marugame, Japan

[21] Appl. No.: 87,160

[22] Filed: Oct. 22, 1979

[30] Foreign Application Priority Data

Oct. 23, 1978 [JP] Japan ............................... 53-130724

[51] Int. Cl.³ ............................................. B02C 4/00
[52] U.S. Cl. .................................... 264/118; 264/141; 264/DIG. 51
[58] Field of Search ........ 264/109, 118, 141, DIG. 51

[56] References Cited

U.S. PATENT DOCUMENTS

| | | | |
|---|---|---|---|
| 3,071,816 | 1/1963 | Allen et al. | 264/144 |
| 3,886,249 | 5/1975 | Manganaro | 264/118 |
| 4,129,633 | 12/1978 | Biddick | 264/DIG. 51 |
| 4,190,622 | 2/1980 | Landis | 264/DIG. 51 |

*Primary Examiner*—Donald E. Czaja
*Assistant Examiner*—James R. Hall
*Attorney, Agent, or Firm*—Thomas R. Morrison

[57] ABSTRACT

A method of producing granular sodium dichloroisocyanurate, comprises the steps of forming thin columnar pellets of sodium dichloroisocyanurate from wet powdery solids thereof obtained in the manufacturing process, drying the pellets to remove free water therein, compacting, crushing and screening. According to this method, granular sodium dichloroisocyanurate in the form of anhydride, monohydrate or dihydrate may be obtained by controlling the temperature and the humidity of heating air used in the drying step.

10 Claims, 1 Drawing Figure

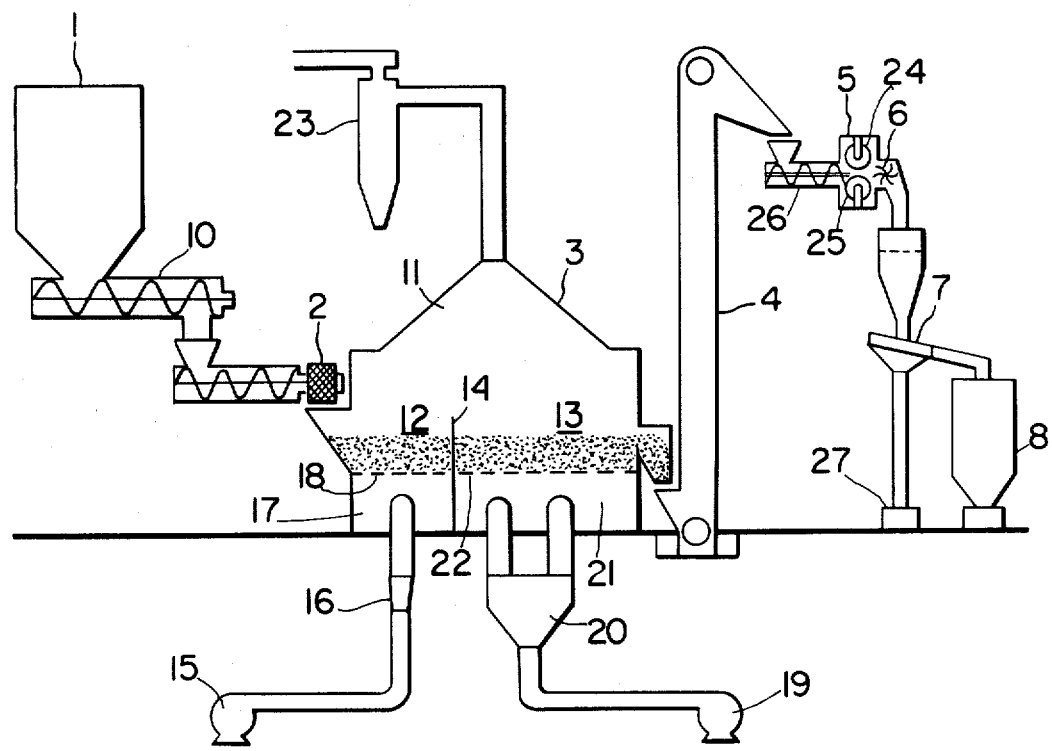

METHOD OF PRODUCING GRANULAR SODIUM DICHLOROISOCYANURATE

BACKGROUND OF THE INVENTION

1. Field of the Invention

The present invention relates to a method of producing granular sodium dichloroisocyanurate from the wet cake thereof obtained in the manufacturing process.

Sodium dichloroisocyanurate has been widely used as a solid chlorine compound which is effective to release active chlorine for various purposes such as for sterilizing water in swimming pools and dirty water such as, for instance, sewerage.

2. Description of the Prior Art

For storage, transportation and use, it is preferable to supply sodium dichloroisocyanurate in the form of granules.

Prior art methods for producing granular sodium dichloroisocyanurate have been disclosed in Japanese Pat. No. 513 484 (Jap. Pat. Publn No. 23 198/1967) granted to the assignee of the present patent application, wherein chloroisocyanuric acid or an alkali metal thereof containing an adjusted amount of water is formed into tablets with a surface pressure of about 1,000 Kg/cm$^2$. The tablets are then crushed. In U.S. Pat. No. 3,886,249 sodium dichloroisocyanurate powder containing an adjusted amount of water for hydration is fed to compactor rolls to form a sheet thereof and the resulting sheet is broken into granules.

The method disclosed in the Japanese patent has the disadvantage that the wet or moisture containing acid or salt has a relatively high viscosity or stickiness which adversely affects the ability to continuously supply it in fixed amounts to a pellet forming machine. In addition, when the tablets are crushed in a granulator to produce uneven dimensional agglomerates, considerable pulverization accompanies the process. Therefore, this method is not suitable for industrially preparing commercial products.

The method of the United States patent has the disadvantage that the sodium dichloroisocyanurate powder containing hydration water is so sticky that it is difficult to continuously supply the material in a fixed amount through a hopper to the sheet forming compactor, because of a so-called "bridging" phenomenon in the hopper which, in turn, produces blocking or jamming. Such blocking or jamming may also cause loss of hydration water due to friction heat and consequently permit chain-reactional thermal decomposition of the sodium dichloroisocyanurate. This method is, therefore, also not suitable for safe and smooth production of the granules on an industrial scale.

OBJECTS AND SUMMARY OF THE INVENTION

Accordingly, a principal object of the present invention is to provide a method of producing granular sodium dichloroisocyanurate, which obviates and overcomes the disadvantages of the prior art.

A specific object of the invention is to provide a method of producing granular sodium dichloroisocyanurate, which makes it possible to carry out a safe and smooth operation in an industrial scale.

Another specific object of the invention is to provide a method of producing granular sodium dichloroisocyanurate, wherein powdering during the granulation step can be reduced to increase the yield of products.

A still further object of the invention is to provide a method of producing granular sodium dichloroisocyanurate, which produce the products in compact form to make handling thereof easy and to increase its ability to disperse and dissolve in water.

According to the invention, the above and other objects, features and advantages of the present invention can be attained by a method of producing granular sodium dichloroisocyanurate, which comprises the steps of extruding wet sodium dichloroisocyanurate through a screen with a plurality of fine openings to form columnar pellets, passing the pellets through a fluidized bed heating chamber to dry the same until they contain substantially no free water, compacting the dried pellets, crushing the compacted pellets, and screening the resulting pellets.

Heated dry air can be fed to the fluidized bed heating chamber to finally obtain sodium dichloroisocyanurate anhydride.

Moisture adjusted hot air can be fed to the fluidized bed heating chamber to obtain sodium dichloroisocyanurate in mono or dihydrated form.

The reason for using moisture adjusted heated air herein is as follows:

Monohydrate and dihydrate of sodium dichloroisocyanurate have their own vapor pressure at various temperatures. Therefore, it is possible to obtain either monohydrate and dihydrate from wet sodium dichloroisocyanurate arbitrarily by conditioning the humidity and temperature of heated air beforehand so as to balance the vapor pressure of waste air with that of the material to be dried.

The compacting and crushing steps may be carried out using a roll type compactor and an impeller type crusher, respectively. The drying of the columnar pellets to remove free water in the fluidized bed heating chamber and the treatment using the rolls and the impeller changes the pellets into small compact granules which rapidly sink in water, do not adhere to one another at the bottom of the water and dissolve in water in a relatively short time period.

BRIEF DESCRIPTION OF THE DRAWING

The drawing shows a schematic illustration of an apparatus suitable for carrying out the method according to the present invention.

DETAILED DESCRIPTION OF THE PREFERRED EMBODIMENT

Raw material of moisture contained sodium dichloroisocyanurate, obtained by any conventional manufacturing process may be used such as, for example, the product made by neutralizing dichloroisocyanuric acid with sodium hydroxide or reacting three components of trichloroisocyanurate, cyanuric acid and sodium hydroxide in a molar ratio of 2:1:3 in water, and then concentrating under reduced pressure or cooling the reaction mixture to separate and gather resulting precipitate.

Referring to the figure, the wet raw material is fed from a raw material tank 1 using a screw feeder 10 and is extruded through a screen extruder type granulator 2 in the form of thin rods. The thin rods break down of their own weight to form columnar pellets which are fed into a fluidized bed type dryer 3. Fluidized bed type dryer 3 includes a drying chamber 11 which includes a first area 12 and a second area 13 separated by a divider 14. A blower 15 blows air through a moisture conditioning and heating element 16 into a region 17 below screen 18 of first area 12.

Similarly, a blower 19 provides air through a moisture conditioning and heating element 20 to a region 21 below a screen 22.

The columnar pellets breaking off from granulator 2 fall into first area 12 where they are supported by the air flowing thereinto through screen 18 and are dried as they move toward divider 14. The columnar pellets continue through second area 13 where they are further dried and/or moisture conditioned by air flowing through screen 22. During drying in dryer 3, the rods or pellets are broken into relatively short columnar pellets of substantially uniform size or length. At least the free water adhered to and contained in the pellets is removed and the total water content thereof is in the desired range.

Waste air from drying chamber 11 is exhausted through a cyclone-type separator 23 for removing dust and fine particles from the waste air. The resulting dried pellets from second area 13 are fed through a vertical conveyor 4 which raises them to a screw-type conveyor 26 feeding a roll type compactor 5 having a pair of rotary rolls 24 and 25, at least one of which has a rough surface to compact the dried pellets against the other roll. The resulting compacted pellets are then crushed in rotating impeller 6 to produce granules. The resulting granules are fed to a vibrating screen 7 for dressing thereof and to obtain the finished product. The finished products are fed from vibrating screen 7 to a receiving hopper 8.

The following are conditions suitable for carrying out the method according to the present invention.

The diameter of each opening in a screen for the screen extruder type granulator 2 is preferably from about 0.5 to about 3.0 mm and more preferably from about 1.5 to about 2.0 mm.

First 12 and second 13 areas of fluidized bed type dryer 3 preferably provide low and high temperature zones. For the production of anhydride, sodium dichloroisocyanurate supplied from granulator 2 is fed into first area 12 maintained at a lower temperature in which the fluidized layer is heated to 50° to 80° C. with heated dry air and then passed to second area 13 which is heated to 80° to 150° C. with heated dry air. For the production of monohydrate, both the first and second areas 12 and 13 are heated uniformly to 70° to 150° C. and more preferably to 75° to 85° C. with moisture controlled heated air. For the production of dihydrate, the first and second areas 12 and 13 are heated uniformly to 50° to 65° C. and more preferably to 60° to 65° C. with moisture controlled heated air. The moisture controlled air preferably contains water in the ratio of about 26 g to 1 Nm$^3$ of dry air.

It is preferable to set the rotational speed of the rolls 24 and 25 of roll type compactor 5 at a low level, for instance, 5 to 50 rpm, and to produce a pressure between the rolls in a range of 500 to 1500 Kg of force per linear centimeter of contact line between rolls 24 and 25.

The water or moisture content of the wet sodium dichloroisocyanurate to be fed to screen extruder type granulator 2 should be in the range of 15 to 30%. If the moisture content is lower than such level, the load on the granulator increases making granulation difficult and a powdering phenomenon appears in the subsequent drying step. If the moisture content is higher than such level, the thin rod-like pellets formed by granulator 2 adhered to one another and form agglomerates in the drying step thus making uniform drying thereof impossible and inhibiting desirable smooth and continuous operation.

The final products of granules recovered in hopper 8 through the treatment by vibrating screen 7 have a size distribution in a range of 10 to 60 mesh, of which the main part lies in a range of 14 to 28 mesh. The average bulk density lies in a range of 0.8 to 1.2 g/cm$^3$. Excessively fine or coarse particles which pass vibrating screen 7 are recovered in receiver 27.

Powdered or fine granules of sodium dichloroisocyanurate recovered from cyclone-type separator 23 and from receiver 27 may be recycling into raw material tank 1 by adding a predetermined amount of water or fresh raw material thereto to regulate the water content therein in preparation for again passing this material through the screen extruder type granulator 2.

The granular products of sodium dichloroisocyanurate anhydride, monohydrate or dihydrate rapidly sink in water, do not adhere to each other in water and dissolve in a relatively short time as stated below.

| Products | Time in second for complete dissolution |
|---|---|
| Anhydride | 80 to 85 |
| Monohydrate | 90 to 95 |
| Dihydrate | 85 to 90 |

In each case, 2 g of the product was added in 1000 ml of water at 20° C.

According to the method of the invention, since the raw wet sodium dichloroisocyanurate is chemically unstable, it is first extruded through the screen extruder type granulator under a low loading pressure and the resulting pellets are dried until they contain substantially no free water. This dried form is chemically stable. The dried, stable intermediate product is then compacted in roll type compactor 5 under a high loading pressure. Therefore, the method ensures complete safety during the entire operation.

EXAMPLE 1

Wet sodium dichloroisocyanurate containing 25% moisture and stored in raw material tank 1 were continuously fed by screw feeder 10 at a rate of 200 Kg/hr to screen extruder type granulator 2 with a screen having a large number of openings, each of which had a diameter of 1.5 mm to extrude therefrom the raw material and to form thin rods which broke off of their own weight to form columnar pellets which fell into first area 12 of drying chamber 11 of fluidized bed dryer 3. In fluidized bed type dryer 3, the pellets were passed through a lower temperature first area 12 having a surface area of 0.15 m$^2$ and heated with hot dry air at 70° to 80° C. for an average time of 5 minutes. The pellets were then passed through a higher temperature second area 13 having a surface area of 0.6 m$^2$ and heated with hot dry air at 125° to 135° C. for an average time of 20 minutes to sufficiently dry the pellets into the anhydride state. The resulting dried pellets were fed through vertical conveyor 4 and a double screw feeder 26 to roll type compactor 5 containing a pair of rolls 24 and 25, each having a diameter of 300 mm and a length of 180 mm and rotating at 15 rpm. The rolls were loaded to produce a pressure therebetween of 1200 Kg per centimeter of linear contact line therebetween to compact the pellets.

The resulting compacted pellets were crushed by rotary impeller 6 and then sieved by vibrating screen 7 to recover granules of 60 or below in mesh size.

In a Reference Example, dried solids of sodium dichloroisocyanurate were compressed in roll type compactor 5 to obtain granules without the steps of forming the columnar pellets and drying them in the manner described.

The size distribution, yield of granules of 60 or below in mesh size, bulk density and dissolving rate (time required for completely dissolving in water when 2 g of the products is added to 1000 ml of water at 20° C.) of the granules obtained by the process described in Example 1 are compared with those of the granules obtained by the process stated in the Reference Example to obtain results shown in Table 1 as follows.

TABLE 1

|  | Example 1 | Reference Example |
|---|---|---|
| Size distribution (%) | | |
| 10-14 mesh | 4.7 | 0.9 |
| 14-28 mesh | 40.2 | 16.7 |
| 28-35 mesh | 5.5 | 14.1 |
| 35-60 mesh | 0.5 | 3.0 |
| above 60 mesh | 49.1 | 65.3 |
| Yield (%) | 50.9 | 34.7 |
| Bulk density (g/cm$^3$) | 0.89 | 0.80 |
| Dissolving rate (sec) | 82 | 86 |

The process described in Example 1 was continuously carried out for 24 hours in which 1830 Kg of product was produced. During 24 hours of operation of the process of the Reference Example, operation was forced to stop twice because of abnormal heat generation due to an overload of the screw-type feeder 26 of the roll type compactor 5. During this 24-hour period, only 1145 Kg of product was produced.

EXAMPLE 2

Wet sodium dichloroisocyanurate containing 25% moisture stored in raw material tank 1 was continuously fed by screw feeder 10 at a rate of 200 Kg/hr to screen extruder type granulator 2 comprising a screen having a large number of openings, each of which has a diameter of 1.5 mm to extrude therefrom the raw material and to form thin rods which broke off of their own weight to form columnar pellets. The pellets were fed to fluidized bed type dryer 3 which had a total surface area of 0.75 m$^2$ (including areas 12 and 13) and in which air heated in a temperature range of 60° to 65° C. and containing moisture of 25.9 g to 1 Nm$^3$ of dry air was continuously supplied and is effective to maintain the temperature of the pellets at from about 50° to about 65° C. The pellets were passed through dryer 3 over an average time of 20 minutes to form dried sodium dichloroisocyanurate in the form of dihydrate.

The dried pellets at this stage had a bulk density of 0.73 g/cm$^3$ and size distribution, as generally shown below.

| below 10 mesh | 22.0 (%) |
|---|---|
| 10-12 (mesh) | 54.8 |
| 12-20 | 15.7 |
| 20-28 | 3.5 |
| 28-60 | 2.0 |
| 60-100 | 0.5 |

| -continued | |
|---|---|
| above 100 mesh | 1.5 |

The resulting dried pellets containing essentially no free water were fed through vertical conveyor 4 and double screw feeder 26 to roll type compactor 5 containing a pair of rolls 24 and 25, each having a diameter of 300 mm and a length of 180 mm rotating at 15 rpm. The rolls were loaded to produce a pressure therebetween of 1200 Kg per linear centimeter of contact line therebetween for compacting the pellets.

The resulting compacted pellets were crushed by rotary impeller 6 and then sieved by vibrating screen 7 to recover granules of 60 or below in mesh size in hopper 8.

As a Reference Example, sodium dichloroisocyanurate powder in the form of dihydrate dried to a state containing no free water was treated with roll type compactor 5 to obtain granules without performing the remaining steps of Example 2.

The size distribution, yield of granules of 60 or below in mesh size, bulk density and dissolving rate of the granules obtained by the process described in Example 2 are compared with those of the granules obtained by the process stated in the Reference Example to obtain the result shown in Table 2 as follows.

TABLE 2

|  | Example 2 | Reference Example |
|---|---|---|
| Size distribution (%) | | |
| 10-14 (mesh) | 14.0 | 5.2 |
| 14-28 | 35.2 | 17.6 |
| 28-35 | 14.0 | 16.3 |
| 35-60 | 11.3 | 10.0 |
| above 60 | 25.5 | 50.9 |
| Yield (%) | 74.5 | 49.1 |
| Bulk density (g/cm$^3$) | 0.96 | 0.92 |
| Dissolving rate (sec) | 95 | 105 |

The process described in Example 2 was continuously carried out for 24 hours during which there was no trouble in obtaining 3,180 Kg of products. During 24 hours of operation of the process of the Reference Example, the bridging phenomenon of the raw material in a hopper of the roll type compactor 5 occurred 16 times. At each occurrence of the bridging phenomenon operation was stopped and the stoppage was corrected manually. The yield of the products during the 24-hour period was limited to 1,900 Kg.

EXAMPLE 3

Wet sodium dichloroisocyanurate containing 25% moisture and stored in raw material tank 1 were continuously fed by a screw feeder 10 at a rate of 200 Kg/hr to screen extruder type granulator 2 comprising a screen having a large number of openings, each of which has a diameter of 1.5 mm to extrude therefrom the raw material and to form thin rods which broke off of their own weight to form columnar pellets. The pellets were fed to fluidized bed type dryer 3 which has a surface area of 0.75 m$^2$ (including area 12 and 13) and in which air heated to a range of 75° to 85° C. and containing moisture of 25.9 g to 1 Nm$^3$ of dry air was continuously supplied and was effective to keep the temperature of the pellets at between 70° and 85° C. The pellets were passed through dryer 3 over an average time of 20 minutes to form sodium dichloroisocyanurate in the form of monohydrate containing essentially no free water.

The resulting dried pellets were compacted by roll type compactor 5, crushed by rotary impeller 6 and sieved by vibrating screen 7 to recover granules of 60 or below in mesh size similar to the method described in Example 2.

As a Reference Example, sodium dichloroisocyanurate powder in the form of monohydrate dried to a state containing no free water was compacted with roll type granulator 5 to obtain granules without performing the remaining steps in the process of Example 3.

The size distribution, yield of granules of 60 or below in mesh size, bulk density and dissolving rate of the granules obtained by the process described in the Example 3 are compared with those of the granules obtained by the process stated in the Reference Example are shown in Table 3 as follows.

TABLE 3

|  | Example 3 | Reference Example |
|---|---|---|
| Size distribution (%) |  |  |
| 10–14 (mesh) | 9.0 | 3.1 |
| 14–28 | 38.1 | 17.8 |
| 28–35 | 9.8 | 14.6 |
| 35–60 | 5.9 | 6.5 |
| above 60 | 37.2 | 58.0 |
| Yield (%) | 62.8 | 42.0 |
| Bulk density (g/cm$^3$) | 0.93 | 0.90 |
| Dissolving rate (sec) | 93 | 105 |

The process described in Example 3 was continuously carried out for 24 hours during which there was no trouble in obtaining 2,445 Kg of products. During 24 hours of operation of the process of the Reference Example, bridging of the raw material in a hopper of roll type compactor 5 occurred 13 times, each of which required ceasing operation and manual correction. The yield of products was limited to 1,435 Kg.

We claim:

1. A method of producing granular sodium dichloroisocyanurate comprising the steps of extruding wet sodium dichloroisocyanurate having a moisture content of about 15–30% through a screen with a plurality of openings to form columnar pellets, passing said pellets through a fluidized bed heating chamber to dry said pellets until they contain substantially no free water, compacting said dried pellets to increase their bulk density, crushing said compacted pellets, and screening the crushed pellets to obtain the granular sodium dichloroisocyanurate product.

2. A method as claimed in claim 1, wherein each of said plurality of openings in said screen has a diameter of from about 0.5 to about 3.0 mm.

3. A method as claimed in claim 1, wherein said fluidized bed heating chamber has low and high temperature zones in which said pellets are heated by hot dry air to a temperature of 50° to 80° C. and 80° to 150° C. respectively to obtain dried pellets of sodium dichloroisocyanurate anhydride.

4. A method as claimed in claim 1, wherein said fluidized heating chamber has a single heating zone in which said pellets are heated uniformly at a temperature of 50° to 150° C. by hot air containing an amount of moisture which is effective to produce hydrated sodium dichloroisocyanurate.

5. A method as claimed in claim 1, wherein said compacting is carried out by a roll type compactor having a pair of rolls which rotate at a rotational frequency of 5 to 50 rpm. and impart a load of 500 to 1,500 Kg per centimeter of contact line therebetween.

6. A method as claimed in claim 1, wherein said crushing is carried out by a rotary impeller.

7. A method as claimed in claim 4, wherein said amount of moisture in said hot air is about 26 g of water to 1 Nm$^3$ of dry air.

8. A method as claimed in claim 4, wherein the temperature of said pellets in said heating zone is from about 70° to about 150° C. to obtain granular sodium dichloroisocyanurate in the form of monohydrate.

9. A method as claimed in claim 4, wherein the temperature of said pellets in said heating zone is from about 50° to about 65° C. to obtain granular sodium dichloroisocyanurate in the form of dihydrate.

10. A method as claimed in claim 1, wherein said granular sodium dichloroisocyanurate has a bulk density of from about 0.8 to about 1.2 gr./cm$^3$.

* * * * *